United States Patent
Valenta, Jr. et al.

(10) Patent No.: US 7,151,378 B2
(45) Date of Patent: Dec. 19, 2006

(54) IMPLANTABLE ENERGY MANAGEMENT SYSTEM AND METHOD

(75) Inventors: Harry L. Valenta, Jr., Aurora, CO (US); Joseph M. Probst, Williamsville, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 361 days.

(21) Appl. No.: 10/253,330

(22) Filed: Sep. 24, 2002

(65) Prior Publication Data

US 2003/0076113 A1    Apr. 24, 2003

Related U.S. Application Data

(60) Provisional application No. 60/324,708, filed on Sep. 25, 2001.

(51) Int. Cl.
  *G01N 27/416* (2006.01)
  *A61N 1/18* (2006.01)

(52) U.S. Cl. .......... 324/426; 324/434; 607/29; 607/34

(58) Field of Classification Search ........ 324/537; 128/899; 320/108, 163, 110, 106, 122, 148, 320/135; 607/37, 116, 33, 61, 57, 5, 60, 607/32; 600/17; 623/3.1

See application file for complete search history.

(56) References Cited

U.S. PATENT DOCUMENTS

| | | | |
|---|---|---|---|
| 3,942,535 A | 3/1976 | Schulman | 607/33 |
| 4,096,866 A | 6/1978 | Fischell | 607/34 |
| 4,665,896 A | 5/1987 | LaForge et al. | 600/17 |
| 5,272,475 A * | 12/1993 | Eaton et al. | 340/7.32 |
| 5,350,413 A | 9/1994 | Miller | 607/61 |
| 5,369,351 A | 11/1994 | Adams | 320/121 |
| 5,411,537 A | 5/1995 | Munshi et al. | 607/33 |
| 5,541,489 A * | 7/1996 | Dunstan | 320/134 |
| 5,554,919 A * | 9/1996 | Uchida | 320/132 |
| 5,591,217 A | 1/1997 | Barreras | 607/61 |
| 5,656,915 A * | 8/1997 | Eaves | 320/118 |
| 5,690,693 A | 11/1997 | Wang et al. | 607/61 |
| 5,702,431 A | 12/1997 | Wang et al. | 607/61 |
| 5,713,936 A * | 2/1998 | Staub et al. | 607/29 |
| 5,713,939 A | 2/1998 | Nedungadi et al. | 607/61 |
| 5,735,887 A | 4/1998 | Barreras, Sr. et al. | 607/33 |
| 5,749,909 A | 5/1998 | Schroeppel et al. | 607/60 |
| 5,767,659 A * | 6/1998 | Farley | 320/106 |
| 5,827,326 A | 10/1998 | Kroll et al. | 607/33 |
| 5,836,973 A | 11/1998 | Kroll | 607/5 |
| 5,903,764 A * | 5/1999 | Shyr et al. | 713/300 |
| 5,959,371 A | 9/1999 | Dooley et al. | 307/130 |
| 5,991,665 A | 11/1999 | Wang et al. | 607/5 |
| 6,067,474 A | 5/2000 | Schulman et al. | 607/57 |
| 6,166,518 A * | 12/2000 | Echarri et al. | 320/106 |

(Continued)

FOREIGN PATENT DOCUMENTS

EP    0 515 059 B1    2/1997

(Continued)

*Primary Examiner*—Anjan Deb
*Assistant Examiner*—John Teresinski
(74) *Attorney, Agent, or Firm*—Hodgson Russ LLP

(57) ABSTRACT

An implantable energy supply system having at least two cells is disclosed. The system may have a switch with a first state in which the cells are electrically connected to a load, and a second state in which each cell is electrically connected with its own charger. A measurer may be electrically connected to a cell to provide an indication of the charge on the cell.

21 Claims, 6 Drawing Sheets

Independent charge - Series Load with Over Current, Over Temperature, and Low Voltage Disconnect and Gas Gauge

U.S. PATENT DOCUMENTS

| | | | |
|---|---|---|---|
| 6,181,105 B1 | 1/2001 | Cutolo et al. | 320/115 |
| 6,227,204 B1 | 5/2001 | Baumann et al. | 128/899 |
| 6,240,318 B1 | 5/2001 | Phillips | 607/61 |
| 6,278,258 B1 | 8/2001 | Echarri et al. | 320/130 |
| 6,288,521 B1 * | 9/2001 | Meador | 320/118 |
| 6,441,584 B1 * | 8/2002 | Crass | 320/131 |
| 6,552,511 B1 * | 4/2003 | Fayram | 320/103 |
| 2002/0076071 A1 * | 6/2002 | Single | 381/312 |

FOREIGN PATENT DOCUMENTS

| | | |
|---|---|---|
| EP | 1 048 324 A2 | 11/2000 |
| EP | 1 166 820 A2 | 1/2002 |
| WO | WO 01/28064 A2 | 4/2001 |
| WO | WO 01/83029 A1 | 11/2001 |

* cited by examiner

Independent charge - Series Load
with Over Current, Over Temperature, and
Low Voltage Disconnect and Gas Gauge

IMPLANTABLE ENERGY MANAGEMENT
SYSTEM AND METHOD

CLAIM OF PRIORITY

This application claims the benefit of U.S. patent application No. 60/324,708 filed on Sep. 25, 2001.

BACKGROUND INFORMATION

The invention relates generally to power sources, and one embodiment of the invention may be used in an implantable medical device. Implantable power sources for medical devices are not new. Many such devices use a rechargeable cell to provide power, and these cells are often lithium-ion cells. The high energy density of a lithium-ion cell results in the dimensions of the power source being smaller than for power sources using different cell-chemistry.

In order to achieve high voltage output, cells of prior art devices are connected in series to a load, such as a defibrillator, left ventricular assist pump, hearing aides or a total artificial heart. When the cells need to be recharged, the load is electrically disconnected from the cells, and a charging power source is electrically connected to the cells. The series-connected cells are then charged, often by a constant current and then by a constant voltage, until they reach a predetermined voltage. Due to the high energy density of lithium-ion cells, the charge and discharge processes must be performed according to precise guidelines. Once charged, the load is re-connected to the cells.

BRIEF DESCRIPTION OF THE DRAWINGS

The nature and objects of the invention will be made clearer with reference to the following detailed description taken in conjunction with the accompanying drawings, in which.

DETAILED DESCRIPTION

Figure 1:
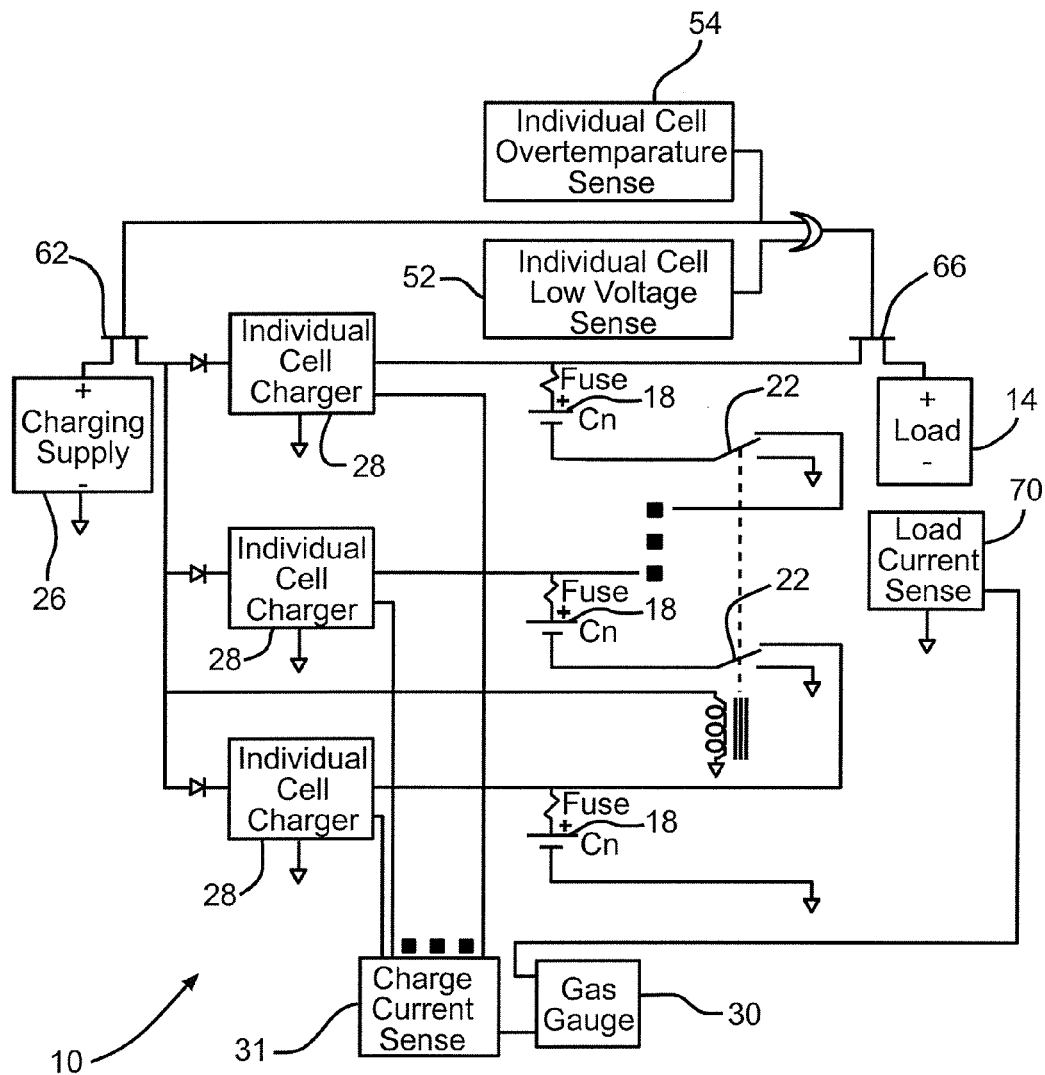
FIG. 1 is a schematic of an embodiment of a device according to the invention.
Figure 2:
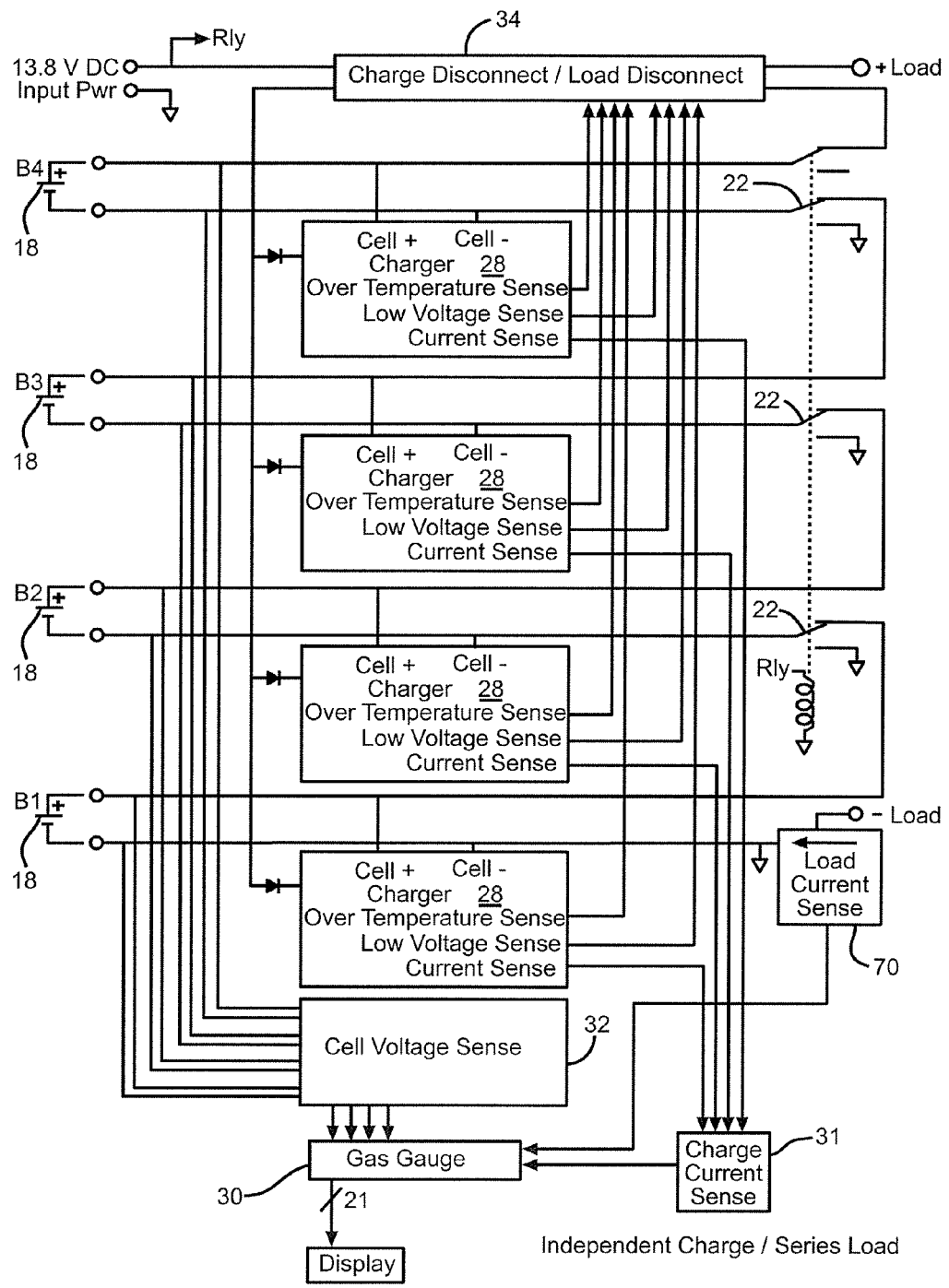
FIG. 2 is a another schematic of the device depicted in FIG. 1.
Figure 3:
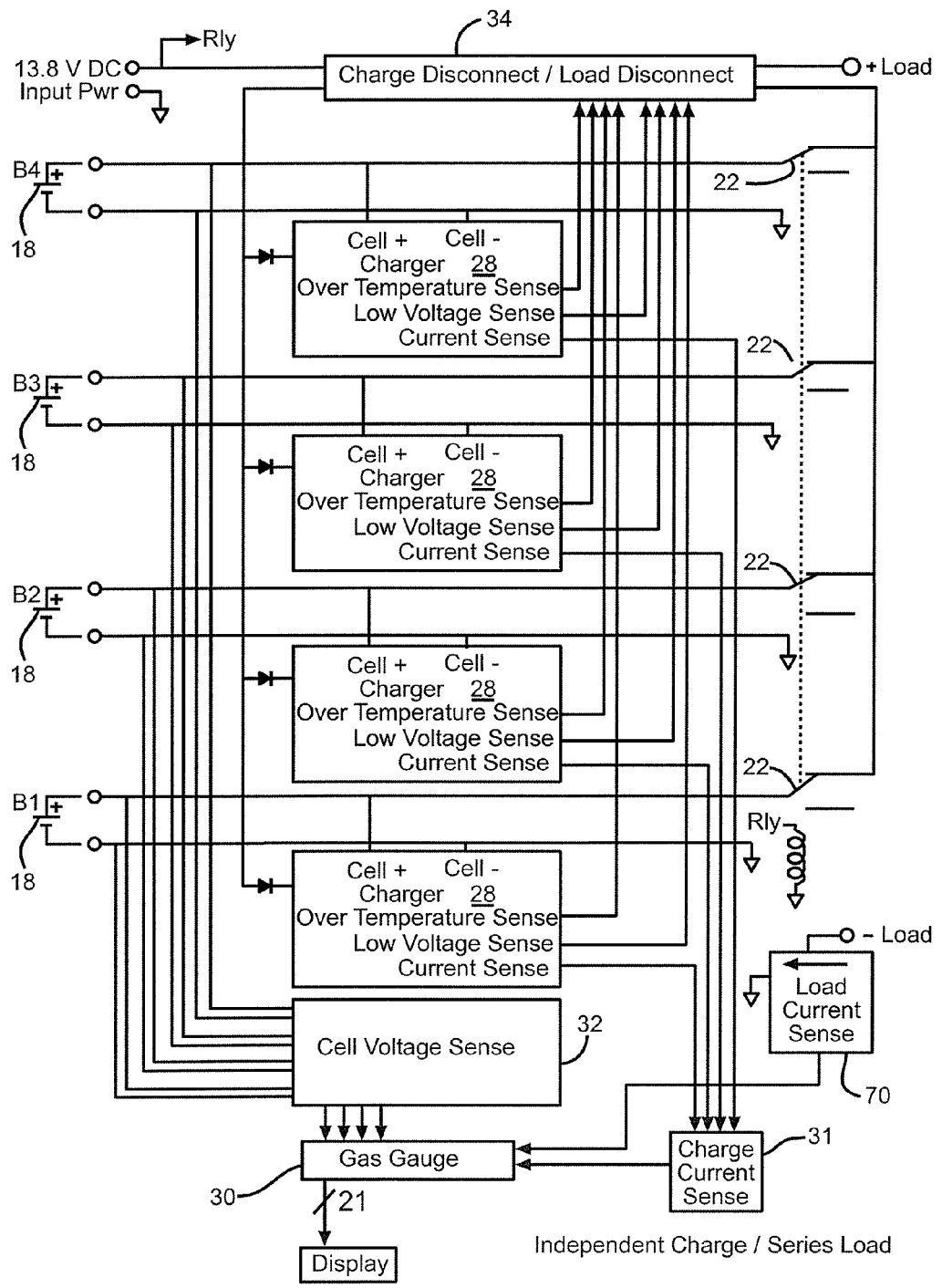
FIG. 3 is a schematic of another device according to the invention.
Figure 4:
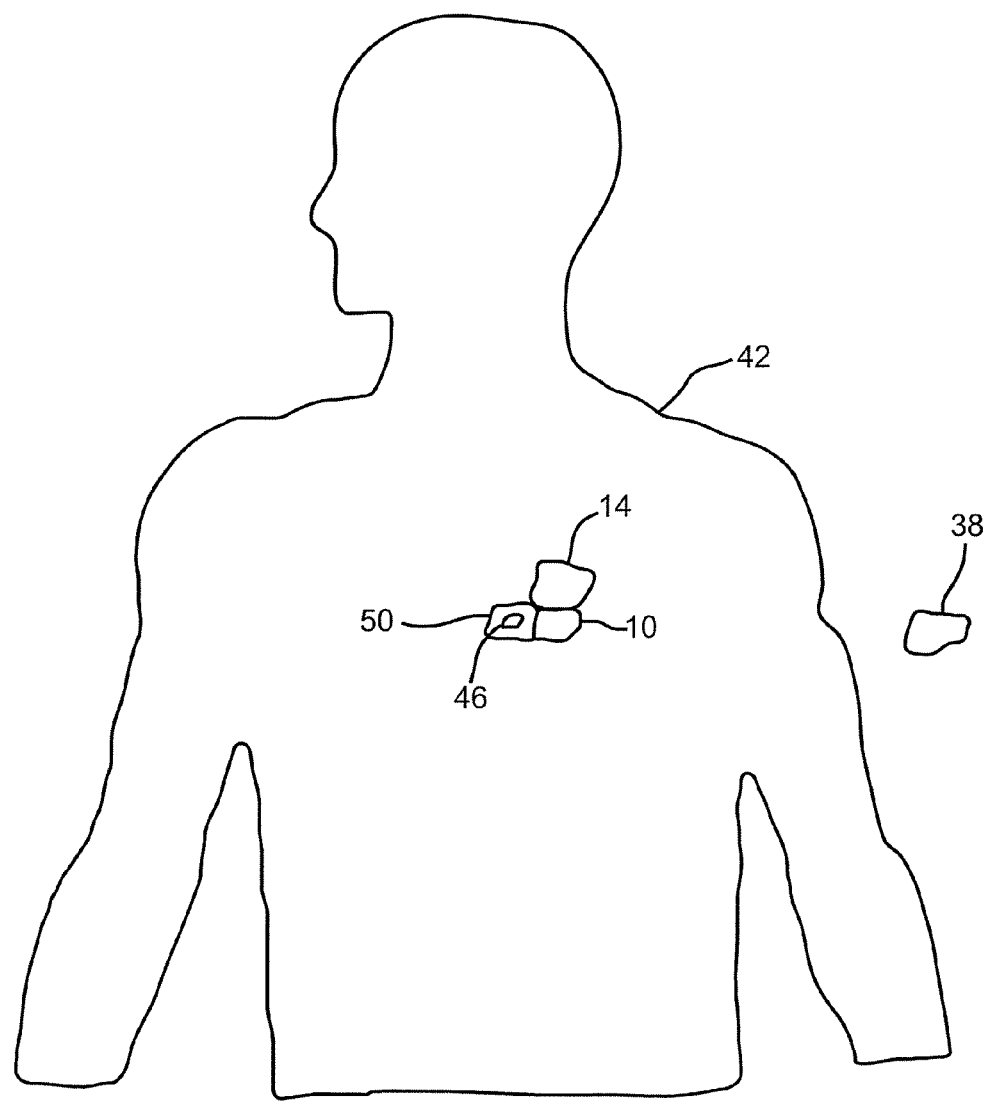
FIG. 4 depicts a device according to the invention inside a human being.

FIGS. 1–3 depict embodiments of an implantable energy supply system 10 according to the invention. The supply system 10 may supply energy to a load 14, such as a ventricular assist pump, hearing assist device, drug pump, neurostimulator, pacemaker, defibrillator or total artificial heart.

The supply system 10 may include at least two cells 18, each of which may be a lithium-ion cell. A switch 22 may be provided, which has a first state in which the cells 18 are electrically connected to a load 14. The cells 18 may be connected in parallel or in series with the load 14. The switch 22 may have a second state in which each cell 18 is electrically connected to its own cell charger 28. The decision to change the switch 22 between the first and second states may be made by a machine, such as a microprocessor, or by a human being. Alternatively, the switch 22 may be biased to the first state and moved to the second state when the cell charger 28 is connected to the cell 18. The switch 22 may be moved between the first and second states by connecting or disconnecting, as the case may be, the cell charger 28 with the corresponding cell 18.

A charge measurer 30 may be electrically connected to one or more of the cells 18. The charge measurer 30 may provide an indication of the charge on a cell 18 so that it can be known whether that cell 18 is at or below a low threshold charge level and therefore in need of charging. The charge measurer 30 may provide an indication of the charge on a cell 18 so that it can be known whether that cell 18 is at or above a high threshold charge level and therefore fully charged. Further, the charge measurer 30 may provide an indication of the charge on a cell 18 so that it can be known whether that cell 18 is between the low threshold and the high threshold charge levels. A charge current sensor 31 may provide to the charge measurer 30 a signal indicating the current being delivered to a cell 18. The charge measurer 30 may include a timer, and when used in conjunction with the signal provided by the charge current sensor 31, the amount of energy delivered to a cell may be determined and used to decide when a cell 18 is adequately charged. A cell voltage sensor 32 may provide to the charge measurer 30 a signal indicating the voltage on a cell. The signal provided by the cell voltage sensor 32 may be used to control the charging process that is managed by the cell charger 28.

The charge measurer 30 may provide an indication of when one or more of the cells 18 may need to be recharged. The energy supply system 10 may include a load current monitor 70, which may provide a signal when the current supplied to the load 14 is below a threshold level, thereby indicating that one or more of the cells 18 may need to be charged. The charge measurer 30 may be equipped to compare the load current at various times during discharge of the cells 18, and from this load current data, predict when a cell or cells 18 should be recharged. This prediction may be provided in the form of a signal so that plans may be made to recharge the cells 18 at a convenient time.

A logic circuit 34 may be electrically connected to the measurer 30. The logic circuit 34 may include a microprocessor or an integrated circuit, or both. The logic circuit 34 may provide signals to disconnect the load from the cells 18 when the indication of the charge on an individual cell 18 is below the low threshold level, or when an indication of the temperature of an individual cell 18 is above a threshold level.

The indication of the charge on a cell 18 may be related to a quantity of energy delivered to the cell 18. For example, the indication of the charge on a cell 18 may be determined from a voltage differential across terminals of the cell 18. The indication of the charge on a cell 18 may be determined from a rate of current delivered to the cell 18 and the length of time the current was delivered.

Energy delivered to the supply system 10 for charging the cells 18 may be transmitted from a source 38 outside an animal's body 42 to a receiver 46 in the charging power source 26 inside the animal's body 42. The receiver may be a coil inside the animal's body 42 that is magnetically coupled with a coil in the source 38. A transformer 50 may include both the receiver 46 and devices for converting the energy into electricity that is usable by the system 10, which may then be supplied to one or more of the cells 18 in order to charge those cells 18. The energy supplied by the source 38 may include radio waves as the primary mode of transmitting the energy to the receiver 46.

Figure 5:
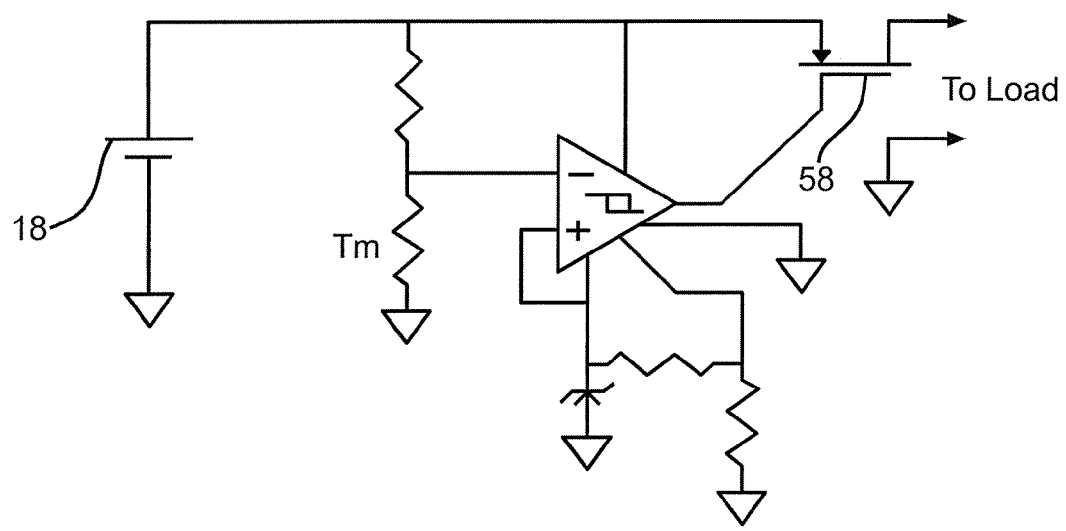
FIG. 5 is a schematic of a circuit that may be used in a device according to the invention.
Figure 6:
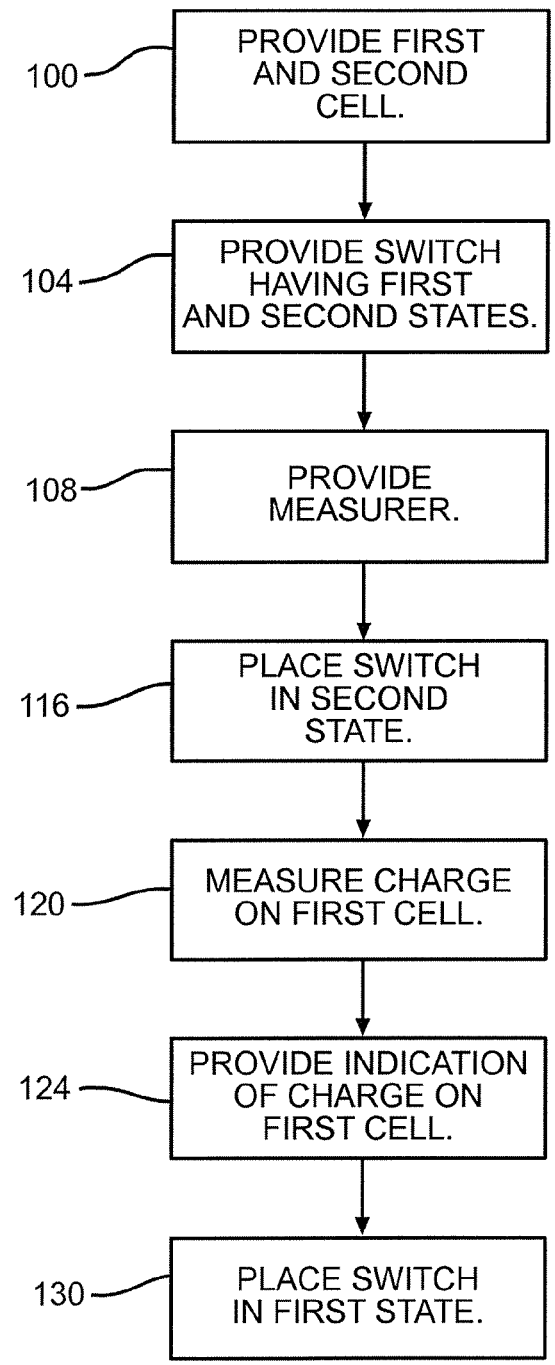
FIG. 6 is a flow chart of a method according to the invention.

The energy supply system 10 may have a low voltage sensor 52. The low voltage sensor 52 may be capable of providing a low voltage signal when the voltage on a cell 18 drops below a threshold level. Further, the energy supply system 10 may have a temperature monitor 54 joined to one or more of the cells 18. The temperature monitor 54 may be capable of providing a high temperature signal when a temperature of a cell 18 exceeds a threshold temperature. A cell switch 58 (see FIG. 5) may receive the low voltage signal or the high temperature signal, and electrically disconnect the corresponding cell 18. In this manner, a cell 18 with a low voltage, a high temperature, or both, may be removed from operation before it causes damage to itself or the rest of the energy supply system 10.

A charging power source switch 62 may receive the high temperature signal and electrically disconnect a charging power source 26. In this manner, the charging power source 26 may be prevented from providing electricity in order to avoid causing damage to the energy supply system 10.

A load switch 66 may receive the low voltage signal, the high temperature signal, or both, and electrically disconnect the load 14 from the energy supply system 10. In this manner, the supply system 10 may be removed from operation before it causes damage.

In a method according to the invention, a first cell and a second cell are provided 100. A switch is provided 104 that has a first state in which the cells are electrically connected to a load, and a second state in which the first cell is electrically connected to its own charger. A measurer is provided 108, which is electrically connected to the first cell. The measurer is capable of providing an indication of the charge on the first cell.

When the indication of the charge indicates the first cell is below a threshold level, the switch may be placed 116 in the second state, whereupon electricity is supplied to the first cell. The charge on the first cell is measured 120 and an indication of the charge is provided 124. When the indication of the charge indicates the first cell is above a threshold level, the switch is placed 130 in the first state.

Although the invention has been described with respect to one or more particular embodiments, it will be understood that other embodiments of the invention may be made without departing from the spirit and scope of the invention.

What is claimed is:

1. An implantable energy supply system, comprising:
   a first cell and a second cell;
   a switch having a first state in which the cells are electrically connected to a load, and a second state in which each cell is electrically connected to its own charger;
   a measurer electrically connected to cell and providing an indication of the charge on each cell.

2. The energy supply system of claim 1, further comprising a logic circuit electrically connected to the measurer and capable of providing signals to disconnect the load from the cells when the first cell requires charging.

3. The energy supply system of claim 1, further comprising a logic circuit electrically connected to a cell temperature sensor and capable of providing signals to disconnect the load from the cells when the first cell has a high temperature.

4. The energy supply system of claim 3, wherein the logic circuit includes a microprocessor.

5. The energy supply system of claim 3, wherein the logic circuit includes an integrated circuit.

6. The energy supply system of claim 1, wherein the indication of the charge on the first cell is a quantity of energy delivered to the first cell.

7. The energy supply system of claim 1, wherein the indication of the charge on the first cell is determined from a voltage differential across terminals of the cell.

8. The energy supply system of claim 1, wherein the indication of the charge on the first cell is determined from a rate of current delivered to the first cell.

9. The energy supply system of claim 1, further comprising a transformer having a receiver to accept energy, and provide electricity to the first cell.

10. The energy supply system of claim 9, wherein the energy includes radio waves.

11. The energy supply system of claim 1, further comprising a temperature monitor joined to one of the cells.

12. The energy supply system of claim 11, wherein the temperature monitor is capable of providing a high temperature signal when a temperature of the one of the cells exceeds a threshold temperature.

13. The energy supply system of claim 12, further comprising a high-temperature switch capable of electrically disconnecting said one of the cells when the high temperature signal is provided.

14. The energy supply system of claim 12, further comprising a high-temperature switch capable of preventing the charging power source from providing electricity to said one of the cells when the high temperature signal is provided.

15. The energy supply system of claim 12, further comprising a high-temperature switch capable of electrically disconnecting a load from the cells when the high temperature signal is provided.

16. The energy supply system of claim 1, further comprising a load current monitor capable of providing a signal when the load current is below a threshold level.

17. The energy supply system of claim 1, wherein when connected to the load, the cells are electrically connected in series.

18. The energy supply system of claim 1, wherein when connected to the load, the cells are electrically connected in parallel.

19. A method of charging cells in an implantable medical device, comprising:
   providing a first cell and a second cell;
   providing a switch having a first state in which the cells are electrically connected to a load, and a second state in which each cell is electrically connected to its own charger;
   providing a measurer electrically connected to each cell and providing an indication of the charge on each cell
   placing the switch in the second state;
   supplying electricity to the first cell;
   measuring a charge on the first cell and providing an indication of the charge;
   placing the switch in the first state when the indication of the charge indicates the cell is charged to a predetermined level.

20. The energy supply system of claim 19, wherein the switch is placed in the second state when the indication of the charge is below a threshold level.

21. The energy supply system of claim 19, wherein the switch is placed in the first state when the indication of the charge is above a threshold level.

* * * * *